United States Patent [19]

Margossian

[11] Patent Number: 4,785,013
[45] Date of Patent: Nov. 15, 1988

[54] FUNGICIDAL COMPOSITION BASED ON IPRODIONE

[75] Inventor: Albert Margossian, Chennevieress, France

[73] Assignee: Rhone-Poulenc Agrochimie, Lyons, France

[21] Appl. No.: 617,836

[22] Filed: Jun. 6, 1984

Related U.S. Application Data

[63] Continuation of Ser. No. 357,669, Mar. 12, 1982, abandoned.

[30] Foreign Application Priority Data

Mar. 20, 1981 [FR] France .................. 81 05798
Feb. 5, 1982 [FR] France .................. 82 02020

[51] Int. Cl.$^4$ ............................ A01N 43/50
[52] U.S. Cl. .................. 514/391; 514/939; 514/941; 514/938
[58] Field of Search .............. 424/273 R; 514/391

[56] References Cited

U.S. PATENT DOCUMENTS

| | | | |
|---|---|---|---|
| 3,657,443 | 4/1972 | Klopping | 424/273 |
| 3,755,350 | 8/1973 | Sauli | 424/273 |
| 4,044,145 | 8/1977 | Lacroix | 424/273 |
| 4,071,685 | 1/1978 | Rentzea et al. | 424/273 |
| 4,305,953 | 12/1981 | Pfiegel et al. | 424/273 |

FOREIGN PATENT DOCUMENTS 2149923 4/1972 Fed. Rep. of Germany .

OTHER PUBLICATIONS

Jones, Chem Abst 83:38622f (1975).
Lacroix et al., Chem Abst. 83:2032z (1975).
Van Assche et al, Chem Abst. 85:88377s (1976).

*Primary Examiner*—Albert T. Meyers
*Assistant Examiner*—F. L. Krosnick
*Attorney, Agent, or Firm*—Emmanuel J. Lobato; Robert E. Burns

[57] ABSTRACT

Composition containing:
a—from 20 to 40% of iprodione,
b—an oil-in-water emulsion containing 50 to 160% by weight, relative to the iprodione, of an oil of which the hydrophilic/lipophilic balance has a value of 9 to 12, and
c—from 0.1 to 2% by weight of an emulsifier of the ethylene oxide/fatty alcohol condensate type.

Composition for the protection of plants against fungal diseases.

18 Claims, No Drawings

FUNGICIDAL COMPOSITION BASED ON IPRODIONE

This is a continuation of application Ser. No. 357,669, filed Mar. 12, 1982, now abandoned.

The present invention relates to a new fungicidal composition based on iprodione.

Iprodione is the well-known name for denoting an agricultural fungicide known by the chemical name of 1-isopropylcarbamoyl-3-(3,5-dichlorophenyl)-hydantoin. This fungicide has an excellent activity against fungal diseases in plants, in particular botrytis in vines.

Hitherto, this active ingredient has been marked essentially in the form of wettable powder. This formulation has the disadvantage of dispersing dust into the atmosphere when it is handled, either whilst it is being put into bags or whilst the wettable powder is being diluted in water during the preparation of the slurry. Furthermore, this formulation can be washed off the surface of the leaves or seeds in the event of heavy rainfall.

The object of the present invention is to overcome these disadvantages. It relates to an agricultural fungicidal composition based on iprodione, which contains, by weight:

a—from 20 to 40% of an active ingredient based on iprodione,
b—an "oil-in-water" emulsion containing 50 to 160% by weight, relative to the iprodione, of an oil of which the hydrophilic/lipophilic balance (HLB) has a value of 8 to 12, and preferably of 10 to 11, on the HLB scale required for the preparation of an "oil-in-water" emulsion,
c—from 0.1 to 2% of a non-ionic emulsifier of the ethylene oxide/fatty alcohol condensate type, and
d—if appropriate, from 0.5 to 2.5% of a substantially neutral, hydrophilic silica,
the remainder to 100% consisting of water and the customary additives.

The compositions according to the invention are concentrated suspensions of iprodione in an oil-in-water emulsion. These fluid formulations are frequently referred to in practice as "fluid pastes", "creams" or "flowables".

In these compositions, the active ingredient is based on iprodione in the form of solid particles which have an average diameter of less than 10 microns, and preferably have an average diameter of 1 to 5 microns.

In these suspensions, apart from the iprodione, the active ingredient can include other active ingredients such as, in particular, carbendazime, benomyl or methyl thiophanate, or a copper-based compound, a metal ethylenebis-dithiocarbamate such as maneb, zineb or mancozeb, or a phthalimide derivative such as captan, captafol or folpet.

However, other mixtures containing iprodione in association with other fungicides can be formulated according to the present invention.

The oil which can be used in the compositions according to the invention can be of a variety of types, provided that it can dissolve from 1 to 5 g of iprodione per liter of oil at ordinary temperature, and provided that its hydrophilic/lipophilic balance (HLB) has a value of 8 to 12, and preferably of 10 to 11, on the HLB scale required for the preparation of an "oil-in-water" emulsion, and that it preferably has a viscosity of between 20 and 30 cst. The hydrophilic/lipophilic balance is defined and determined according to "Pesticide formulation"—Wade Van Valkenburg—published by Marcel Dekker Inc.—New York 1973.

These oils can be mineral oils such as refined petroleum oils, commonly referred to as white oils, with a boiling range of between 300 to 400° C. at atmospheric pressure, and having a high proportion of paraffinic hydrocarbons with, preferably, a minimum proportion of 92% of materials which cannot be sulphonated. Certain vegetable oils, of which the hydrophilic/lipophilic balance has a value within the range defined above, can also be used, such as e.g. groundnut oil, maize germ oil or colza oil.

Another important constituent of the composition according to the invention is a particular emulsifier of the ethylene oxide/fatty alcohol condensate type, which is a condensate of one or more linear or branched $C_{12}$ to $C_{14}$ and preferably $C_{13}$ fatty alcohols with from 8 to 12 mols and preferably from 9 to 10 mols of ethylene oxide, and which provides the stability of the concentrated suspension of iprodione in the oil-in-water emulsion by acting both as a dispersing-wetting agent for the iprodione and as an emulsifier for the binary "oil-water" system.

In certain cases, if it is desired to reduce the amount of oil in order to reduce any possible phytotoxicity, without detracting from the biological properties of the formulation, it can be advantageous to add 0.5 to 2.5% by weight of a preferably substantially neutral, hydrophilic silica to the formulation. In the context of the invention, the term "hydrophilic silica" is understood as meaning a preferably synthetic silica such as an ultrafine hydrated precipitated silica with a high specific surface area of the order of 200 to 300 $m^2/g$, measured according to the B.E.T. method. A silica of this type is substantially neutral, i.e. its pH in aqueous suspension is 7±0.5. In practice, a neutral or weakly acidic silica is preferred.

The compositions according to the invention can also contain conventional adjuvants such as viscosity modifiers (in general from 0.05 to 0.1% by weight) of the polysaccharide type, in particular heteropolysaccharides resulting from the fermentation of carbohydrates by a microorganism of the xanthomonas type, dispersingfluidising agents of the ethylene oxide/polyarylphenol condensate type, preferably in the acid phosphate form (in general from 0.5 to 2.5% by weight), anti-freeze agents such as ethylene glycol or propylene glycol (in general from 5 to 10% by weight), anti-foam agents such as silicone oil emulsions (generally from 0.2 to 0.6% by weight), and preservatives for combating microbial proliferations (in general from 0.1 to 0.2% by weight), such as formaldehyde.

The compositions according to the invention can be prepared e.g. in three steps.

The first step consists in preparing the "oil-in-water" emulsion in a tank equipped with a means of vigorous agitation, by running the oil into the water containing the other water-soluble additives and, if appropriate, the emulsifier.

In a second step, the iprodione, as a fine powder, is dispersed in the oily emulsion with continued agitation. The suspension obtained is then refined in a mill, e.g. of the ball mill type such as the DYNO-MILL.

In the third and final step, the viscosity modifier of the heteropolysaccharide type is dispersed in a small amount of water containing the preservative (40% strength aqueous solution of formaldehyde) and/or the neutral hydrophilic silica. This dispersion is incorporated into the suspension of iprodione described above.

Apart from having the advantage of being fluid formulations, which are easier to handle than wettable powders, the oily compositions of iprodione according to the invention have the advantage of an enhanced fungicidal efficacy when they are applied in a spraying treatment for combating fungal diseases in plants (vines, lettuces, tomatoes, strawberry plants, trees bearing small fruits, and the like) and in particular for combating botrytis (*Botrytis cinerea*), without exhibiting phytotoxicity.

The examples which follow are given, without implying a limitation, in order to illustrate the compositions according to the invention and their noteworthy biological properties.

EXAMPLE 1

A concentrated oily suspension is prepared which has the following percentage composition by weight:
iprodione with a particle diameter of the order of 2 microns: 25.0
paraffinic mineral oil containing more than 70% of paraffin, having a hydrophilic/lipophilic balance with a value of 10.5, and solubilizing 1 g of iprodione per liter: 33.0
emulsifier based on condensates of 9-10 mols of ethylene oxide with synthetic $C_{13}$ alcohols: 0.8
phosphate of ethylene oxide/polystyrylphenol condensate: 2.5
ethylene oxide/polyalkylphenol condensate: 0.5
ethylene glycol: 5.0
heteropolysaccharide (Rhodopol 23): 0.065
formaldehyde (40% strength aqueous solution): 0.15
silicone oil emulsion: 0.5
water: q.s.p. 100

Firstly, the water, the glycol, the silicone emulsion and the surface-active agents, including the emulsifier, are mixed in a tank. The mixture is agitated until total dispersion has taken place, and the oil is then run into the mixture.

The iprodione is then added with continued agitation. An emulsion is obtained which is ground in a DYNO-MILL to give a concentrated suspension of iprodione.

In the third and final step, the viscosity modifier (heteropolysaccharide), predispersed in a small amount of water containing the preservative (40% strength formaldehyde solution), is incorporated into the suspension of iprodione to give, finally, a fluid paste or concentrated dispersion which is ready for use.

EXAMPLE 2

According to the process of Example 1, a concentrated oily suspension is prepared which has the following percentage composition by weight:
iprodione: 30.0
mineral oil containing more than 70% of paraffin, having a hydrophilic/lipophilic balance with the value of 10, and dissolving 1.2 g of iprodione per liter of oil: 20.0
ethylene glycol: 5.0
condensates of 8-10 mols of ethylene oxide with synthetic $C_{13}$ alcohols: 0.8
acid phosphate of ethylene oxide/polystyrylphenol condensate: 1.2
silicone oil emulsion: 0.5
synthetic neutral hydrophilic silica (B.E.T. surface area: 200 m$^2$/g): 2.0
water: q.s.p. 100

EXAMPLE 3

According to the process of Example 1, a concentrated oily suspension is prepared which has the following percentage composition by weight:
iprodione: 37.5
mineral oil containing more than 70% of paraffins and having a hydrophilic/lipophilic balance with a value of 11 and dissolving 1 g iprodione per liter of oil: 20.0
ethylene glycol: 5.0
condensates of 9-10 mols of ethylene oxide with synthetic $C_{13}$ alcohols: 1.0
acid phosphate of ethylene oxide/polystyryl phenol condensate: 1.5
silicon oil emulsion: 0.5
neutral hydrophilic precipitated silica (B.E.T. surface area: 300 m$^2$/g): 1.25
water: q.s.p. 100

EXAMPLE 4

According to the process of Example 1, a concentrated oily suspension is prepared which has the following percentage composition by weight:
iprodione: 37.5
industrial groundnut oil solubilizing 3.5 g of iprodione per liter: 20.0
ethylene glycol: 5.0
condensates of 9-10 mols of ethylen oxide with synthetic $C_{13}$ alcohols: 1.0
acid phosphate of ethylene oxide/polystyrylphenol condensate: 2.0
silicone oil emulsion: 0.5
neutral hydrophilic silica: 1.0
water: q.s.p. 100

EXAMPLE 5

According to the process of Example 1, a concentrated oily suspension is prepared which has the following percentage composition by weight:
iprodione: 26.0
paraffinic mineral oil (containing more than 70% of paraffin, having an HLB value of 10.5 and solubilizing 4.5 g of iprodione per liter: 32.2
emulsifier based on condensates of 9-10 mols of ethylene oxide with synthetic $C_{13}$ alcohols: 0.8
phosphate of ethylene oxide/polystyrylphenol condensate: 2.5
ethylene oxide/polyalkylphenol condensate: 0.5
propylene glycol: 5.0
heteropolysaccharide (Rhodopol 23): 0.65
formaldehyde (40% strength aqueous solution): 1.5
water: q.s.p. 100

EXAMPLE 6

According to the process of Example 1, a concentrated oily suspension is prepared which has the following percentage composition by weight and in which the iprodione is associated with another active ingredient, carbendazime, and the adjuvants are identical to those of Example 5:
iprodione: 18.0
carbendazime: 9.5
paraffinic mineral oil: 28.0
emulsifier based on condensates of 9-10 mols of ethylene oxide with synthetic $C_{13}$ alcohols: 0.8
phosphate of ethylene oxide/polystyrylphenol condensate: 2.5 ethylene oxide/polyalkylphenol condensate: 0.5
propylene glycol: 5.0
heteropolysaccharide (Rhodopol 23): 1.3
formaldehyde (40% strength aqueous solution: 3.0
water: q.s.p. 100

EXAMPLE 7

Open-air fungicide tests on *Botrytis cinerea* in vines

These tests were carried out on 50 m² vine plots by applying, for comparison purposes, an equal dose per hectare of a commercial wettable powder containing 50% by weight of iprodione, and of a composition according to Example 1, according to the following treatment program:

First treatment

When the flower caps fall, in order to purify the dehydrated flower parts which can remain attached to the seeds and protect the stalk.

Second treatment

Before the bunch fills out, i.e. as long as it is still possible to reach the stalk by spraying, in order to protect it against a premature attack of rot.

Third treatment

When ripening starts, i.e. as from the time when the fruit becomes sensitive to attach by botrytis, which is responsible for grey rot in vines.

Fourth treatment

About three weeks before the vintage, in order to ensure that the harvest is in a healthy condition, at a period when the physiological and climatic conditions are frequently very favorable for the development of the fungus.

These treatments were carried out by pneumatic spraying at a low volume/hectare, i.e. from 100 to 300 liters/ha, directed towards the area of the bunches (localized applications) and at a dose per treatment of 750 g of active ingredient per hectare.

Contamination by botrytis took place naturally in the course of the months of September and October, which were damp with frequent night fogs.

Of course, some plots are left without treatment to act as controls.

When harvesting, the level of rot in the fruit, compared with control plots of contaminated and untreated vines, is evaluated.

Under these conditions, it was observed that:
the plots of untreated control vines were attacked with an intensity of 41%, and
the commercial composition of iprodione as a 50% strength wettable powder has an average efficacy or protection of 34%, whereas the composition according to Example 1, applied at the same dose of active ingredient/hectare, effects a protection of 61%.

Furthermore, the composition according to Example 1 proved to be totally selective on vines.

EXAMPLE 8

Open-air fungicide tests on Botrytis cinerea in beans

These tests were carried out on 5 m² plots planted with beans, by applying, for comparison purposes, an equal dose per hectare of a commercial wettable powder containing 50% by weight of iprodione, and of a composition according to Example 1, according to the following program, each treatment being carried out, by pneumatic spraying at a low volume/ha (from 100 to 300 liters/ha), at a dose of 750 g/ha.

First treatment: when flowering starts.
Second treatment: when flowering ends.
Some plots are left without treatment to act as controls.

Contamination took place naturally.

Under these conditions, it is found when harvesting that:
the control plots were attacked to the extent of about 27%,
the plots treated with iprodione as a wettable powder were attacked to the extent of about 15%, and
the plots treated with iprodione formulated according to the invention were attached to the extent of only 4.5%.

EXAMPLE 9

Test for rain resistance 15 cm high Eurocross B tomato plants are sprayed respectively with iprodione as a commercial wettable powder of 50% strength by weight, and with iprodione formulated as in Example 1, the two formulations being applied at the same dose of 375 g of active ingredient per 1,000 liters. The leaves are left to dry. A few plants are then subjected to different levels of artificial rainfall with the aid of a rain-simulating apparatus. Leaf samples are taken for each case of rainfall, inoculated with buffers of *Botrytis cinerea* mycelium and then left to incubate for 4 days at 20° C. in an illuminated atmosphere saturated with moisture. Attack by the disease is then checked.

Under these conditions, it is observed that:
a—as from watering with 5 mm of rainfall, the controls are completely contaminated,
b—for 5 mm of rainfall, the samples treated with iprodione as a wettable powder are attacked to the extent of 56% in contrast to only 36% for those treated with iprodione formulated according to the invention, and
c—for 10 mm of rainfall, the samples treated with iprodione as a wettable powder are attacked to the extent of 87% in contrast to only 31% for those treated with iprodione formulated according to the invention.

The examples clearly show the significant and surprising improvement made to the efficacy of iprodione by using the compositions according to the invention.

I claim:

1. An agricultural fungicidal composition comprising a concentrated suspension of iprodione in an oil-in-water emulsion which contains, by weight:
   a. as an active ingredient from 20 to 40% of iprodione,
   b. 50 to 160% by weight, relative to the iprodione, of an oil of which the hydrophilic/lipophilic balance (HLB) has a value of 8 to 12 on the scale of HLB values for the preparation of an "oil-in-water" emulsion,
   c. from 0.1 to 2% of a non-ionic emulsifier of the ethylene oxide/fatty alcohol condensate type, and
   d. optionally, from 0.5 to 2.5% of a substantially neutral, hydrophilic silica.

2. The composition according to claim 1, wherein the oil has a hydrophilic/lipophilic balance with a value of 10 to 11.

3. The composition according to claim 1, wherein the oil is a mineral oil.

4. The composition according to claim 1, wherein the oil is a vegetable oil.

5. The composition according to claim 1, wherein the non-ionic emulsifier is a condensate of one or more fatty alcohols containing from 12 to 14 carbon atoms with 8 to 12 mols of ethylene oxide.

6. The composition according to claim 5, wherein the emulsifier is a condensate of fatty alcohols containing 13 carbon atoms with 9-10 moles of ethylene oxide.

7. The composition according to claim 1, which contains said silica and wherein the silica is a hydrated precipitated silica having a B.E.T. specific surface area of 200 to 300 m²/g.

8. The composition according to claim 1, wherein said oil has a viscosity of 20 to 30 cst.

9. The composition according to claim 1, in which said iprodione is in the form of solid particles having an average diameter of less than 10 microns.

10. The composition according to claim 1, wherein said iprodione is in the form of solid particles having an average diameter of 1 to 5 microns.

11. The composition according to claim 1, wherein said oil is a mineral oil or a vegetable oil and said non-ionic emulsifier is a condensate of one or more fatty alcohols containing from 12 to 14 carbon atoms with 8 to 12 mols of ethylene oxide.

12. The composition of claim 11, wherein said oil has a viscosity of 20 to 30 cst. and iprodione is in the form of solid particles having an average diameter of less than 10 microns.

13. A composition according to claim 1, wherein the oil can dissolve from 1 to 5 g. of iprodione per liter.

14. A composition according to claim 2, wherein the oil can dissolve from 1 to 5 g. of iprodione per liter.

15. The agricultural fungicidal composition according to claim 1 wherein said active ingredient consists of 20 to 40% of iprodione as the sole active fungicide in the composition.

16. The agricultural fungicidal composition according to claim 1 which is flowable and which consists essentially of, by weight:

20 to 40% of iprodione as the active ingredient,
50 to 160% by weight relative to the iprodione of said oil,
0.1 to 2% of a non-ionic emulsifier which is a condensate of one or more fatty alcohols containing 12 to 14 carbon atoms with 8 to 12 mols of ethylene oxide,
optionally, from 0.5 to 2.5% of a substantially neutral, hydrophilic silica,
0.05 to 0.1% of a polysaccharide viscosity modifier,
0.05 to 2.5% of a dispersing-fluidizing agent which is an acid phosphate of a condensate of ethylene oxide and polyarylphenol,
5 to 10% of an antifreeze agent,
0.2 to 0.6% of a silicone oil anti-foam agent, and
0.1 to 0.2% of preservative.

17. The agricultural fungicidal composition according to claim 1 which is flowable and which consists essentially of, by weight:

20 to 40% of iprodione as the active ingredient,
50 to 160% by weight relative to the iprodione of said oil,
0.1 to 2% of a non-ionic emulsifier which is a condensate of one or more fatty alcohols containing 12 to 14 carbon atoms with 8 to 12 mols of ethylene oxide,
about 0.5 to 2.5% of a substantially neutral, hydrophilic silica,
about 0.05 to 0.1% of a polysaccharide viscosity modifier,
about 0.05 to 2.5% of a dispersing-fluidizing agent which is an acid phosphate of a condensate of ethylene oxide and polyarylphenol,
about 5 to 10% of an antifreeze agent,
about 0.2 to 0.6% of a silicone oil anti-foam agent, and
about 0.1 to 0.2% of preservative.

18. A process for controlling fungal infection of crops, which comprises applying to the crops the composition according to claim 1 in an amount effective to control fungal infection.

* * * * *